(12) United States Patent
Malherbe et al.

(10) Patent No.: US 7,351,700 B2
(45) Date of Patent: Apr. 1, 2008

(54) AMINOMETHYLPYRIMIDINES AS ALLOSTERIC ENHANCERS OF THE GABA$_B$ RECEPTORS

(75) Inventors: Pari Malherbe, Muttenz (CH); Raffaello Masciadri, Basel (CH); Eric Prinssen, Guebwiller (FR); Will Spooren, Franken (FR); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 571 days.

(21) Appl. No.: 11/064,046

(22) Filed: Feb. 23, 2005

(65) Prior Publication Data

US 2005/0197337 A1   Sep. 8, 2005

(30) Foreign Application Priority Data

Mar. 2, 2004   (EA) ................ 04100830.1

(51) Int. Cl.
C07D 239/38 (2006.01)
A61K 31/506 (2006.01)

(52) U.S. Cl. ............... 514/211.15; 514/217.06; 514/218; 514/235.8; 514/252.14; 514/269; 540/472; 540/544; 540/575; 540/601; 544/122; 544/295; 544/315; 544/316

(58) Field of Classification Search ........... 544/122, 544/295, 315, 316; 540/472, 544, 575, 601; 514/211.15, 217.06, 218, 235.8, 252.14, 269
See application file for complete search history.

(56) References Cited

U.S. PATENT DOCUMENTS 6,313,146 B1   11/2001   Van Wagenen et al.

FOREIGN PATENT DOCUMENTS

| WO | WO 95/10506 | 4/1995 |
| WO | WO 01/56990 | 8/2001 |
| WO | WO 02/083651 | 10/2002 |
| WO | WO 03/090731 | 11/2003 |

OTHER PUBLICATIONS

Hill et al., Nature, 290, 149-152, 1981.
Billinton et al., Trends Neurosci., 24, 277-282, 2001.
Bowery et al., Pharmacol. Rev. 54, 247-264, 2002.
Vacher et al.,, Curr. Drug Target, CNS Neurol. Disord. 2, 248-259, 2003.
Bettler, et al., Physiol Rev. 84, 835-867, 2004.
Kaupmann et al.,Nature, 386, 239-246, 1997.
Kaupmann et al., Nature, 396, 683-687, 1998.
Pin et al., Pharmaco. Ther. 98, 325-354, 2003.
Galvez et al., J. Biol. Chem., 275, 41166-41174, 2000.
Havlickova et al., Mol. Pharmacol. 62, 343-350, 2002.
Kniazeff et al.,J. Neurosci., 22, 7352-7361, 2002.
Schuler et al., Neuron, 31, 47-58, 2001.
Peters et al., Neurogenetics, 2, 47-54, 1998.
Mondabon et al., Am. J. Med. Genet 122B/1, 134, 2003.
Gassmann et al., J. Neurosci, vol. 24, pp. 6086-6097, 2004.
Misgeld et al., Prog. Neurobiol. 46, 423-462, 1995.
Enna et al., Life Sci, 62, 1525-1530, 1998.
McCarson et al., Neuropharmacology, 38, 1767-1773, 1999.
Brebner et al., Neuropharmacology, 38, 1797-1804, 1999.
Paterson et al., Psychopharmacology, 172, 179-186, 2004.
Breslow et al., Am. J. Psychiatry, 146, 353-356, 1989.

(Continued)

Primary Examiner—Deepak Rao
(74) Attorney, Agent, or Firm—George W. Johnston; Patricia S. Rocha-Tramaloni; Kimberly J. Prior

(57) ABSTRACT

The present invention relates to compounds of formula

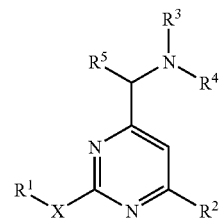

I wherein
X is —S— or —NH—;
$R^3/R^4$ together with the N-atom to which they are attached form a non aromatic 5, 6 or 7 membered ring, which optionally contains in addition to the N-atom one additional heteroatom selected from the group consisting of O, S and N, and wherein the ring is optionally substituted by hydroxy, lower alkyl, lower alkoxy, —NR$_2$, —CONR$_2$, —CO-lower alkyl or benzyl; or $R^3/R^4$ form together with the N-atom to which they are attached a heterocyclic ring system, containing two or three rings and which optionally contains one or two additional heteroatoms selected from the group consisting of N and O and which has no more than 20 carbon atoms; and
R, $R^1$, $R^2$, and $R^5$ are as defined herein and to pharmaceutically suitable acid addition salts thereof.

It has been found that the compounds of the invention are active on the GABA$_B$ receptor and therefore are useful for the treatment of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastro-intestinal disorders.

24 Claims, No Drawings

OTHER PUBLICATIONS

Drake et al., Ann. Pharmacother. 37, 1177-1181, 2003.
Bortolato et al., Psychopharmacology, 171, 322-330, 2004.
Urwyler et al., Mol. Pharmacol., 60, 963-971, 2001.
Pin et al., Mol. Pharmacol.,60, 881-884, 2001.
Binet et al., J Biol Chem., 279, 29085-29091, 2004.
Mombereau et al., Neuropsychopharmacology, vol. 29, 1050-1062, 2004.
Urwyler et al., J. Pharmacol. Exp. Ther., 307, 322-330, 2003.
Cryan et al., J Pharmacol Exp Ther., 310, 952-963, 2004.
Smith et al., Psychopharmacology, 173, 105-111, 2004.
Knoflach et al., Proc. Natl. Acad. Sci., USA, 98, 13402-13407, 2001.
Wichmann et al., Farmaco, 57, 989-992, 2002.
Hammerland et al., Mol. Pharmacol., 53, 1083-1088, 1998.
O'Brien et al., J. Pharmaco. Exp. Ther., 309, 568-577, 2004.
Schaffhauser et al., Mol. Pharmacol., 64, 798-810, 2003.
Porter et al., Br. J. Pharmacol. vol. 128, pp. 13-20 (1999).

AMINOMETHYLPYRIMIDINES AS ALLOSTERIC ENHANCERS OF THE GABA$_B$ RECEPTORS

FIELD OF THE INVENTION

The invention relates to enhancement of GABA$_B$ receptors. The invention further relates to the treatment of CNS disorders, such as anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders or gastro-intestinal disorders, and, respectively, for the manufacture of corresponding medicaments.

BACKGROUND OF THE INVENTION

γ-Aminobutyric acid (GABA), the most abundant inhibitory neurotransmitter, activates both ionotropic GABA$_{A/C}$ and metabotropic GABA$_B$ receptors (Hill and Bowery, *Nature*, 290, 149-152, 1981). GABA$_B$ receptors that are present in most regions of the mammalian brain on presynaptic terminals and postsynaptic neurons are involved in the fine-tuning of inhibitory synaptic transmission. Presynaptic GABA$_B$ receptors through modulation of high-voltage activated Ca$^{2+}$ channels (P/Q- and N-type) inhibit the release of many neurotransmitters. Postsynaptic GABA$_B$ receptors activates G-protein coupled inwardly rectifying K+ (GIRK) channel and regulates adenylyl cyclase (Billinton et al., *Trends Neurosci.*, 24, 277-282, 2001; Bowery et al., *Pharmacol. Rev.* 54, 247-264, 2002). Since the GABA$_B$ receptors are strategically located to modulate the activity of various neurotransmitter systems, GABA$_B$ receptor ligands hence could have potential use as therapeutics in the treatment of anxiety, depression, epilepsy, schizophrenia and cognitive disorders (Vacher and Bettler, *Curr. Drug Target, CNS Neurol. Disord.* 2, 248-259, 2003; Bettler et al., *Physiol Rev.* 84, 835-867, 2004).

Native GABA$_B$ receptors are heteromeric structures composed of two types of subunits, GABA$_B$R1 and GABA$_B$R2 subunits (Kaupmann et al., *Nature,* 386, 239-246, 1997 and *Nature,* 396, 683-687, 1998). The structure of GABA$_B$R1 and R2 show that they belong to a family of G-protein coupled receptors (GPCRs) called family 3. Other members of the family 3 GPCRs include the metabotropic glutamate (mGlu1-8), calcium-sensing, vomeronasal, pheromone and putative taste receptors (Pin et al., *Pharmaco. Ther.* 98, 325-354, 2003). The family 3 receptors (including GABA$_B$ receptors) are characterized by two distinctly separated topological domains: an exceptionally long extracellular amino-terminal domain (ATD, 500-600 amino acids), which contains a venus flytrap module for the agonist binding (orthosteric site) (Galvez et al., *J. Biol. Chem.*, 275, 41166-41174, 2000) and the 7TM helical segments plus intracellular carboxyl-terminal domain that is involved in receptor activation and G-protein coupling. The mechanism of receptor activation by agonist in GABA$_B$R1R2 heterodimer is unique among the GPCRs. In the heteromer, only GABA$_B$R1 subunit binds to GABA, while the GABA$_B$R2 is responsible for coupling and activation of G-protein (Havlickova et al., *Mol. Pharmacol.* 62, 343-350, 2002; Kniazeff et al.,*J. Neurosci.*, 22, 7352-7361, 2002).

Schuler et al., *Neuron*, 31, 47-58, 2001 have demonstrated that the GABA$_B$R1 knock-out (KO) mice exhibit spontaneous seizures and hyperalgesia. These KO mice have lost all the biochemical and electrophysiological GABA$_B$ responses. Interestingly, the GABA$_B$R1 KO mice were more anxious in two anxiety paradigm, namely the light-dark box (decreased time in light) and staircase tests (decreased rears and steps climbed). They showed a clear impairment of passive avoidance performance model indicating impaired memory processes. The GABA$_B$R1 KO also displayed increased hyperlocomotion and hyperactivity in new environment. The GABA$_B$R1 gene is mapped to chromosome 6p21.3, which is within the HLA class I, a region with linkage for schizophrenia, epilepsy and dyslexia (Peters et al., *Neurogenetics,* 2, 47-54, 1998). Mondabon et al., *Am. J. Med. Genet* 122B/1, 134, 2003 have reported about a weak association of the Ala20Val polymorphism of GABA$_B$R1 gene with schizophrenia. Moreover, Gassmann et al., *J Neurosci.* 24, 6086-6097, 2004 has shown that GABA$_B$R2KO mice suffer from spontaneous seizures, hyperalgesia, hyperlocomotor activity and severe memory impairment, comparable to GABA$_B$R1KO mice. Therefore, heteromeric GABA$_B$ R1R2 receptors are responsible for these phenotypes.

Baclofen (Lioresal®, β-chlorophenyl GABA), a selective GABA$_B$ receptor agonist with EC$_{50}$=210 nM at native receptor, is the only ligand, which has been used since 1972 in clinical study for the treatment of spasticity and skeletal muscle rigidity in patients following spinal cord injury, multiple sclerosis, amyotrophic lateral sclerosis, cerebral palsy. Most of the preclinical and clinical studies conducted with baclofen and GABA$_B$ receptor agonists were for the treatment of neuropathic pain and craving associated with cocaine and nicotine (Misgeld et al., *Prog. Neurobiol.* 46, 423-462, 1995; Enna et al., *Life Sci,* 62, 1525-1530, 1998; McCarson and Enna, *Neuropharmacology,* 38, 1767-1773, 1999; Brebner et al., *Neuropharmacology,* 38, 1797-1804, 1999; Paterson et al., *Psychopharmacology,* 172, 179-186, 2004). In panic disorder patients, Baclofen was shown to be significantly effective in reducing the number of panic attacks and symptoms of anxiety as assessed with the Hamilton anxiety scale, Zung anxiety scale and Katz-R nervousness subscale (Breslow et al., *Am. J. Psychiatry,* 146, 353-356, 1989). In a study with a small group of veterans with chronic, combat-related posttraumatic stress disorder (PTSD), baclofen was found to be an effective and well-tolerated treatment. It resulted in significant improvements in the overall symptoms of PTSD, most notably the avoidance, emotional numbing and hyperarousal symptoms and also in reduced accompanying anxiety and depression (Drake et al., *Ann. Pharmacother.* 37, 1177-1181, 2003). In preclinical study, baclofen was able to reverse the reduction in prepulse inhibition (PPI) of the acoustic startle response induced by dizocilpine, but not by apomorphine in rat PPI model of psychosis (Bortolato et al., *Psychopharmacology,* 171, 322-330, 2004). Therefore, GABA$_B$ receptor agonist has a potential in the pharmacological therapy of psychotic disorders. Unfortunately, Baclofen has a number of side-effects disadvantages including the poor blood-brain-barrier penetration, very short duration of action and narrow therapeutic window (muscle relaxation, sedation and tolerance) that limit its utility.

Urwyler et al., *Mol. Pharmacol.,* 60, 963-971, 2001 have reported on a novel class of GABA$_B$ receptor ligands, called positive allosteric modulators, CGP7930 [2,6-di-tert-butyl-4-(3-hydroxy-2,2-dimethyl-propyl)-phenol] and its aldehyde analogue CGP13501. These ligands have no effect on their own at GABA$_B$ receptors, but in concert with endogenous GABA, they increase both the potency and maximal efficacy of GABA at the GABA$_B$R1R2 (Pin et al., *Mol.*

Pharmacol.,60, 881-884, 2001). Interestingly, recent study with CGP7930 (Binet et al., *J Biol Chem.*, 279, 29085-29091, 2004) has shown that this positive modulator activates directly the seven transmembrane domains (7TMD) of GABA$_B$R2 subunit. Mombereau et al., *Neuropsychopharmacology*, 1-13, 2004 have recently reported on the anxiolytic effects of acute and chronic treatment with the GABA$_B$ receptor positive modulator, GS39783 (N,N_-dicyclopentyl-2-methylsulfanyl-5-nitro-pyrimidine-4,6-diamine) (Urwyler et al., *J. Pharmacol. Exp. Ther.*, 307, 322-330, 2003) in the light-dark box and elevated zero maze test models of anxiety. Because the GABA$_B$ enhancers have no effect on receptor activity in the absence of GABA, but do enhance allosterically the affinity of the GABA$_B$ receptor for the endogenous GABA, it is expected that these ligands should have an improved side effect profile as compared to baclofen. Indeed, GS39783 at 0.1-200 mg/kg, PO had no effect on spontaneous locomotor activity, rotarod, body temperature and traction test in comparison to baclofen, which showed these side effects at 2.5-15 mg/kg, PO. GS39783 did not have any effect on cognition performance as assessed by passive avoidance behavioral test in mice and rats. Furthermore, GS39783 exhibited anxiolytic-like effects in the elevated plus maze (rat), elevated zero maze (mice and rats), and the stress-induced hyperthermia (mice) test paradigms. Therefore, GS39783 represents a novel anxiolytic without side-effects associated with baclofen or benzodiazepines (Cryan et al., *J Pharmacol Exp Ther.*, 310, 952-963, 2004). The preclinical investigation with the CGP7930 and GS39783 has shown that both compounds were effective at deceasing cocaine self-administration in rats (Smith et al., *Psychopharmacology*, 173, 105-111, 2004). The positive modulator, CGP7930 has also been preclinically studied for the treatment of Gastro-Esophageal Reflux Disease (GERD) and was found to be effective (WO 03/090731, Use of GABA$_B$ receptor positive modulators in gastro-intestinal disorders).

Positive allosteric modulators have been reported for other family 3 GPCRs including mGlu1 receptor (Knoflach et al., *Proc. Natl. Acad. Sci., USA,* 98, 13402-13407, 2001; Wichmann et al., *Farmaco,* 57, 989-992, 2002), Calcium-sensing receptor (NPS R-467 and NPS R-568) (Hammerland et al., *Mol. Pharmacol.,* 53, 1083-1088, 1998) (U.S. Pat. No. 6,313,146), mGlu2 receptor [LY487379, N-(4-(2-methoxyphenoxy)-phenyl-N-(2,2,2-trifluoroethylsulfonyl)-pyrid-3-ylmethylamine and its analogs] (WO 01/56990, Potentiators of glutamate receptors) and mGlu5 receptor (CPPHA, N-{4-chloro-2-[(1,3-dioxo-1,3-dihydro-2H-isoindol-2-yl)methyl] phenyl}-2-hydroxybenzamide) (O'Brien et al., *J. Pharmaco. Exp. Ther.,* 27, Jan. 27, 2004). Interestingly, it has been demonstrated that these positive modulators bind to a novel allosteric site located within the seven transmembrane domains (7TMD), thereby enhancing the agonist affinity by stabilizing the active state of the 7TMD region (Knoflach et al., *Proc. Natl. Acad. Sci., USA* 98, 13402-13407, 2001; Schaffhauser et al., *Mol. Pharmacol.,* 64, 798-810, 2003). Moreover, the NPS R-467, NPS R-568 (Tecalcet) and related compounds represent the first positive allosteric modulators that entered the clinical trails due to their allosteric mode of action.

SUMMARY OF THE INVENTION

The present invention provides compounds of formula I and pharmaceutically acceptable acid addition salts thereof. In particular, the present invention provides compounds of formula

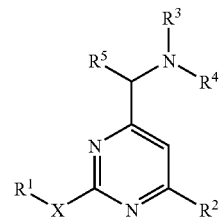

wherein
X is —S— or —NH—;
R$^1$ is alkyl, alkenyl, arylalkyl, arylalkenyl or aryl-O-alkyl, wherein the aryl groups are optionally substituted by one or more substituents, selected from the group consisting of lower alkyl, lower alkoxy, halogen or lower halogenalkyl;
R$^2$ is hydrogen, lower alkyl or cycloalkyl;
R$^3$/R$^4$ together with the N-atom to which they are attached form a non-aromatic 5, 6 or 7 membered ring, which optionally contains in addition to the N-atom one additional heteroatom selected from the group consisting of O, S and N, and wherein the ring is optionally substituted by hydroxy, lower alkyl, lower alkoxy, —NR$_2$, —CONR$_2$, —CO-lower alkyl or benzyl; or
R$^3$/R$^4$ together with the N-atom to which they are attached form a heterocyclic ring system, containing two or three rings, which optionally contains one or two additional heteroatoms selected from the group consisting of N and O, and has no more than 20 carbon atoms;
R$^5$ is hydrogen or alkyl;
R is hydrogen or lower alkyl;

and to pharmaceutically suitable acid addition salts thereof.
The present invention also provides pharmaceutical compositions containing a therapeutically effective amount of one or more compound of the invention and a pharmaceutically acceptable excipient.

The present invention further provides methods for preparing of the compounds of the invention and salts thereof, as well as methods for preparing pharmaceutical compositions of the invention containing a compound of the invention, e.g. a compound of formula I or a pharmaceutically acceptable acid addition salt thereof.

The compounds of formula I and their salts are distinguished by valuable therapeutic properties. It has been found that the compounds are active on the GABA$_B$ receptor. Thus, the present invention also provides methods for treating illnesses in which the GABA$_B$ receptor plays some role, especially illnesses and disorders of the kind referred to earlier, such as anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders or gastro-intestinal disorders.

DETAILED DESCRIPTION OF THE INVENTION

The following definitions of the general terms used in the present description apply irrespective of whether the terms in question appear alone or in combination.

As used herein, the term "alkyl" denotes a straight- or branched-carbon chain group containing from 1 to 12 carbon atoms, for example, methyl, ethyl, pentyl, hexyl, octyl, nonyl and the like.

The term "lower alkyl" denotes a straight- or branched-chain alkyl group containing from 1 to 7 carbon atoms. Preferred lower alkyl groups contain from 1 to 4 carbon atoms.

As used herein, the term "alkenyl" denotes a straight- or branched-carbon chain group containing from 2 to 12 carbon atoms and at least one double bond, for example, ethenyl, propenyl, isopropenyl, butenyl and the like.

As used herein, the term "arylalkyl" or "arylalkenyl" denotes an unsaturated aromatic ring, for example phenyl or naphthyl, which is bound to an alkyl or alkenyl carbon chain as defined above.

The term "halogen" denotes chlorine, iodine, fluorine and bromine.

The term "lower halogen-alkyl" denotes a lower alkyl group as defined above, which is substituted by one or more halogen atoms.

The term "lower alkoxy" denotes a group wherein the alkyl residue is as defined above and the alkyl group is connected via an oxygen atom.

The term "cycloalkyl" denotes a carbon ring with 3 to 6 carbon atoms, preferred is cyclopropyl.

The term "aryl-O-alkyl" denotes an unsaturated aromatic ring, for example phenyl or naphthyl, attached to an alkyl group as defined above through an oxygen atom.

The term "5, 6 or 7 membered ring, which optionally contains in addition to the N-atom an additional heteroatom selected from the group consisting of O, S and N" denotes a non aromatic ring, for example pyrrolidin, piperidin, morpholin, thiomorpholin, 1-oxo- thiomorpholin, 1,1-di-oxo-thiomorpholin, piperazin, 1,4-diazepane, 1,4-ox-azepane or the like.

The term "wherein $R^3$ and $R^4$ form together with the N-atom a heterocyclic ring system, containing two or three rings, which optionally contains one or two additional heteroatoms selected from the group consisting of N and O, and which has no more than 20 carbon atoms" denotes for example the following groups:

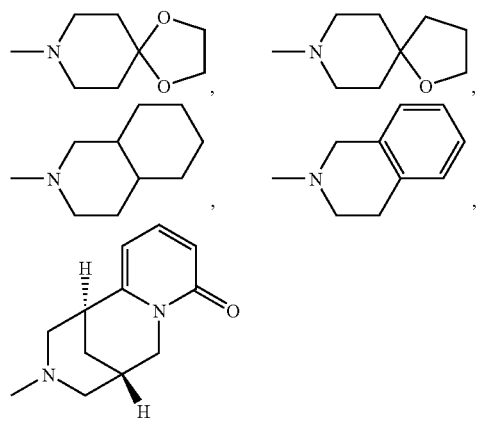

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" denotes an amount that is effective to prevent, alleviate or ameliorate symptoms of disease or prolong the survival of the subject being treated.

The present invention provides compounds of formula I and pharmaceutically acceptable acid addition salts thereof. In particular, the present invention provides a compound of formula

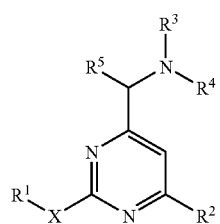

I wherein
X is —S— or —NH—;
$R^1$ is alkyl, alkenyl, arylalkyl, arylalkenyl or aryl-O-alkyl, wherein the aryl groups are optionally substituted by one or more substituents, selected from the group consisting of lower alkyl, lower alkoxy, halogen or lower halogen-alkyl;
$R^2$ is hydrogen, lower alkyl or cycloalkyl;
$R^3/R^4$ together with the N-atom to which they are attached form a non-aromatic 5, 6 or 7 membered ring, which optionally contains in addition to the N-atom one additional heteroatom selected from the group consisting of O, S and N, and wherein the ring is optionally substituted by hydroxy, lower alkyl, lower alkoxy, —NR$_2$, —CONR$_2$, —CO-lower alkyl or benzyl; or
$R^3/R^4$ together with the N-atom to which they are attached form a heterocyclic ring system, containing two or three rings, which optionally contains one or two additional heteroatoms selected from the group consisting of N and O, and which has no more than 20 carbon atoms;
$R^5$ is hydrogen or alkyl;
R is hydrogen or lower alkyl;

or a pharmaceutically suitable acid addition salt thereof.

Preferred compounds of the present invention are those, wherein X is —S—, particularly compounds where $R^3$ and $R^4$ for together with the N-atom a five, six, or seven membered ring which optionally contains an additional N-heteroatom or O-heteroatom. Especially preferred compounds from this group are those, wherein $R^1$ is alkyl and $R^3$ and $R^4$ form together with the N-atom a five or six membered ring which optionally contains an additional O-heteroatom, and which is unsubstituted or substituted by lower alkyl.

Preferred compounds from this group are those, wherein $R^3$ and $R^4$ form together with the N-atom a morpholine ring, for example the following compounds:
4-(2-hexylsulfanyl-6-methyl-pyrimidin-4-ylmethyl)-morpholine, 4-(6-methyl-2-pentylsulfanyl-pyrimidin-4-ylmethyl) -morpholine,
4-(2-hexylsulfanyl-6-trifluoromethyl-pyrimidin-4-ylmethyl)-morpholine,
4-(2-hexylsulfanyl-6-ethyl-pyrimidin-4-ylmethyl)-morpholine and
4-[1-(2-hexylsulfanyl-6-methyl-pyrimidin-4-yl)-ethyl]-morpholine.

Also preferred are compounds from this group wherein $R^1$ is alkyl and $R^3$ and $R^4$ form together with the N-atom a five or six membered ring which optionally contains an additional N-heteroatom. Preferred compounds from this group are futher those, wherein $R^3$ and $R^4$ form together with the N-atom a pyrrolidine or piperidine ring, which is optionally substituted by lower alkyl, for example the following compounds:
2-hexylsulfanyl-4-methyl-6-pyrrolidin-1-ylmethyl-pyrimidine,
2-hexylsulfanyl-4-methyl-6-(2-methyl-piperidin-1-ylmethyl) -pyrimidine,
4-(2,6-dimethyl-piperidin-1-ylmethyl)-2-hexylsulfanyl-6-methyl-pyrimidine and
4-(cis-2,6-dimethyl-piperidin-1-ylmethyl)-2-hexylsulfanyl-6-methyl-pyrimidine.

Other preferred compounds from this group are those wherein $R^3$ and $R^4$ form together with the N-atom a piperazine ring, for example, the following compounds:
4-(4-Ethyl-piperazin-1-ylmethyl)-2-hexylsulfanyl-6-methyl-pyrimidine; and
4-(3,5-Dimethyl-piperazin-1-ylmethyl) -2-hexylsulfanyl-6-methyl-pyrimidine.

Preferred compounds of the present invention are further those, wherein $R^1$ is arylalkyl, optionally substituted by lower alkyl and $R^3$ and $R^4$ form together with the N-atom a five or six membered ring which optionally contains an additional O-heteroatom, for example the following compound:
4-[2-(4-tert-butyl-benzylsulfanyl)-6-methyl-pyrimidin-4-ylmethyl]-morpholine.

Preferred compound of the present invention are further those, wherein $R^1$ is arylalkenyl and $R^3$ and $R^4$ form together with the N-atom a five or six membered ring which optionally contains an additional O-heteroatom, for example, the following compounds:
4-[2-(4-Methoxy-benzylsulfanyl)-6-methyl-pyrimidin-4-ylmethyl]-morpholine;
4-[6-Methyl-2-(4-methyl-benzylsulfanyl)-pyrimidin-4-ylmethyl]-morpholine;
4-[2-(4-tert-Butyl-benzylsulfanyl)-6-methyl-pyrimidin-4-ylmethyl]-morpholine; and
4-[6-Methyl-2-(3-phenyl-propylsulfanyl)-pyrimidin-4-ylmethyl]-morpholine.

Preferred compound of the present invention are further those, wherein $R^1$ is aryl-O-alkyl and $R^3$ and $R^4$ form together with the N-atom a five or six membered ring which optionally contains an additional O-heteroatom, for example, the following compound:
4-[6-Methyl-2-(4-phenoxy-butylsulfanyl)-pyrimidin-4-ylmethyl]-morpholine.

Further preferred are compounds, wherein $R^3$ and $R^4$ form together with the N-atom a heterocyclic ring system, containing two or three rings and which optionally contains one or two additional heteroatoms selected from the group consisting of N and O and which has no more than 20 carbon atoms, for example the following compound:

(1S,5S)-3-(2-Hexylsulfanyl-6-methyl-pyrimidin-4-ylmethyl)-1,2,3,4,5,6-hexahydro-1,5-methano-pyrido[1,2-a][1,5]diazocin-8-one.

Compounds of formula I, wherein $R^5$ is hydrogen are most preferred.

A further object of the present invention is further compounds, wherein $R^5$ is alkyl, particularly methyl or compounds where X is —NH—.

The afore-mentioned compounds of formula I can be manufactured in accordance with the invention by the following process variants:

a) reacting a compound of formula

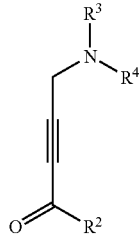

V with a compound of formula

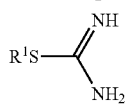

VI-a to produce a compound of formula

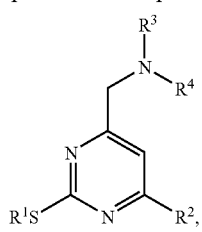

Ia wherein $R^1$ to $R^4$ are as described above, or b) reacting a compound of formula

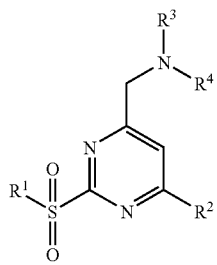

with an amine of formula

to produce a compound of formula

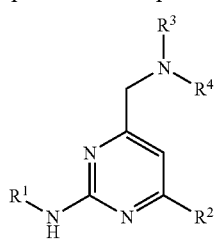

Ib wherein $R^1$ to $R^4$ are as described above, or c) reacting a compound of formula

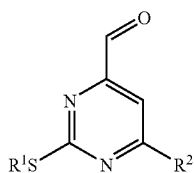

with an amine of formula

HNR³R⁴II to give a compound of formula Ia

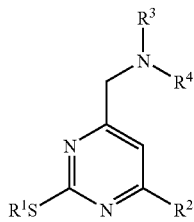

wherein R¹ to R⁴ are as described above, or d) reacting a compound of formula

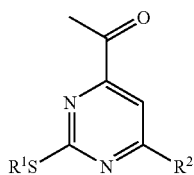

with an amine of formula

HNR³R⁴II to give a compound of formula Ic

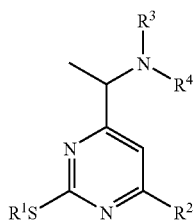

wherein R¹ to R⁴ are as described above, and if desired, converting the compound of formula I obtained into a pharmaceutically acceptable salt.

In the following the preparation of compounds of formula I is described in more detail:

In schemes 1-4 are described processes for preparation of compound of formula I, starting from known compounds, from commercial products or from compounds, which can be prepared in conventional manner.

The preparation of compounds of formula I are further described in detail in working examples 1-43.

In the process description, the following abbreviations have been used:

TEA=triethylamine
THF=tetrahydrofuran
OXONE®=potassium monopersulfate triple salt
DCM=4-(dicyanomethylene)-2-methyl-6-(4-dimethylaminostyryl)-4H-pyran
DMF=N,N-dimethylformamide Scheme 1

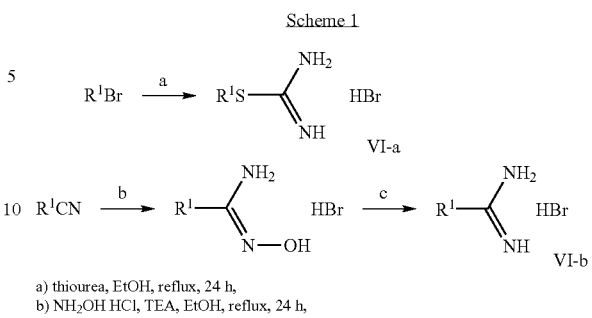

a) thiourea, EtOH, reflux, 24 h,
b) NH₂OH HCl, TEA, EtOH, reflux, 24 h,
c) MsOH, RaNi, EtOH, H₂, 3 h.

In accordance with scheme 1, the intermediates of formulas VI-a and VI-b may be prepared as follows:

Step a:
Thiourea and a corresponding compound of formula R¹Br, for example 1-bromohexane, are heated at reflux under nitrogen in an alcohol, for example ethanol, for about 20 h. The alcohol is evaporated, and after usual isolation and purification the corresponding isothiourea hydrobromide of formula VI-a is obtained.

Step b:
A cyanide of formula R¹CN and hydroxylamine hydrochloride are dissolved in an alcohol, for example in ethanol, and treated with triethylamine. After isolation and purification the corresponding N-hydroxy-amidine is obtained.

Step c:
To a solution of the N-hydroxy-amidine, obtained in step b and an alcohol, for example ethanol, is added fresh Raney Nickel and methanesulfonic acid (MsOH). The reaction mixture is stirred for about 3 h at room temperature in a hydrogen atmosphere. After isolation and purification the corresponding amidine mesylates are obtained.

Scheme 2

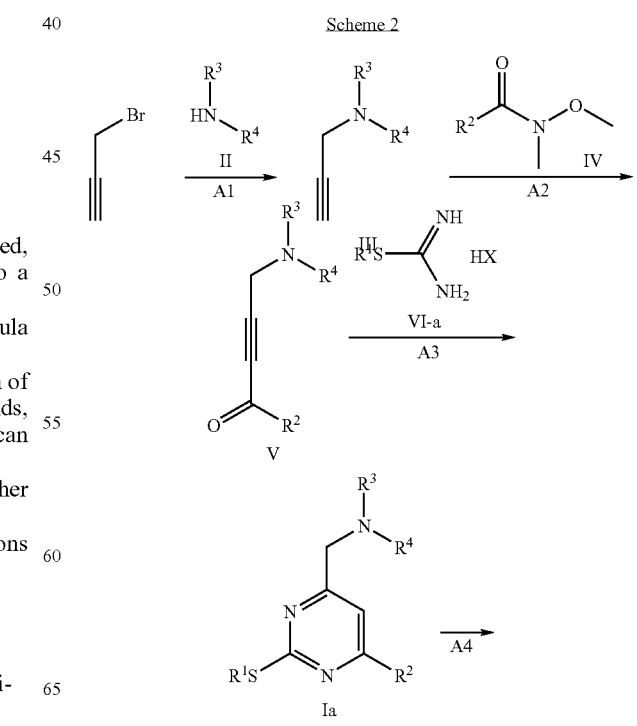

-continued

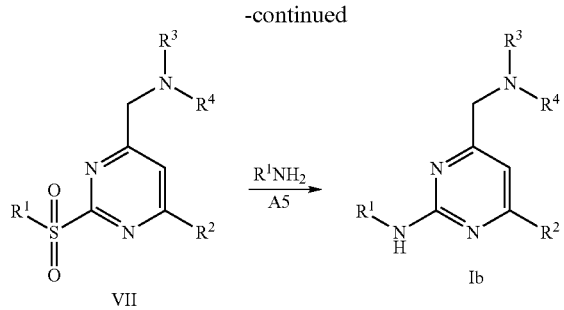

VII

A1) K₂CO₃, MeOH, 0–20° C.,
A2) iPrMgCl, THF, -20° C. or BuLi, THF -70° C.,
A3) TEA, THF, 20° C. or NaOMe, MeOH,
A4) OXONE® (potassium monopersulfate triple salt), MeOH,
A5) THF, 20° C.

In accordance with scheme 2, the intermediates of formulas VI-a and VI-b may be prepared as follows:

Intermediate Compounds of Formula IV:

N,O-dimethyl-hydroxylamine HCl is suspended under nitrogen in DCM and cooled in ice. Triethylamine is added slowly, then acetyl chloride is added slowly, the temperature reached about 20° despite ice cooling and slow addition. Stirring without cooling is continued for about 30 min. After extraction and purification N-methoxy-N-methyl-acetamide is obtained.

or

N,O-dimethyl-hydroxylamine HCl is suspended under nitrogen in DCM and cooled in ice. Triethylamine is added slowly, then cyclopropanecarbonyl chloride is added slowly. Stirring without cooling is continued for 1 h. Extraction: 2×DCM, 1×1 N HCl, 1×NaCl. Distillation: 75° C./20 mbar. One obtained cyclopropanecarboxylic acid methoxy-methyl-amide.

Step A1:

A compound of formula HNR³R⁴ (II), for example morpholine, is dissolved in an alcohol, for example in MeOH, and cooled in ice under nitrogen, then potassium carbonate and propargyl bromide are added while stirring in ice. Stirring without cooling was continued for about 4 h. The obtained suspension is worked up in usual manner. One obtained a compound of formula III, for example 4-prop-2-ynyl-morpholine.

Step A2:

The compound obtained in step A1 is dissolved under nitrogen in THF and cooled to about –40° C. Then a solution of isopropyl magnesium chloride in THF is added while keeping the temperature below –20° C. Stirring at –40° to –30° C. is continued for about 30 min. In a separate flask, a compound of formula IV, for example N-methoxy-N-methylacetamide, is dissolved under nitrogen in THF and cooled to –10° C. in ice/MeOH. The Grignard solution prepared above was transferred to the Weinreb amide solution at –10° C. via teflon tubing under slightly positive nitrogen pressure in vessel 1. Stirring at –10° to 0° C. is continued for about 2 h. The resulting suspension is worked up in usual manner. One obtained a compound of formula V, for example 5-morpholin-4-yl-pent-3-yn-2-one.

Step A3:

The compound obtained in step A2, for example 5-morpholin-4-yl-pent-3-yn-2-one, and a compound of formula VI-a, for example 2-hexyl-isothiourea hydrobromide, are dissolved under nitrogen in DMF, then N,N-diisopropyl ethylamine is added and stirring at the room temperature continued for about 18 hours. The resulting suspension is worked up in usual manner. One obtained a compound of formula Ia, for example 4-(2-hexylsulfanyl-6-methyl-pyrimidin-4-ylmethyl)-morpholine.

Step A4:

The compound of formula Ia obtained in step A3, for example 4-(2-hexylsulfanyl-6-methyl-pyrimidin-4-ylmethyl)-morpholine is dissolved in MeOH and treated with potassium monopersulfate triple salt (OXONE®) for about 2 h. One obtained a compound of formula VII, for example 4-(2-hexylsulfonyl-6-methyl-pyrimidin-4-ylmethyl) -morpholine.

Step A5:

A compound of formula VII, obtained in step A4, and an amine of formula R¹NH₂, dissolved in THF are stirred at 20° C. over night. One obtained a compound of formula Ib.

Scheme 3

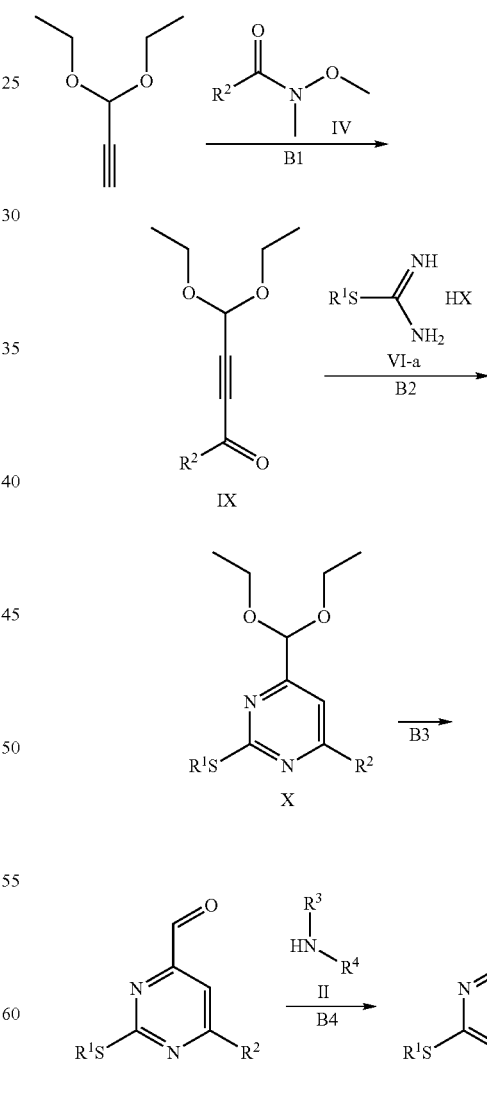

B1) BuLi, THF -70° C. to -30° C.,
B2) TEA, THF, 20° C.,
B3) 4N HCl or TFA/H₂O,
B4) NaBH₃CN or pyBH₃, EtOH/AcOH 10:1, 20° C. or Ti(OiPr)₄, neat, NaBH₃CN, iPrOH In accordance with scheme 3, compounds of formula Ia may be prepared as follows:

Step B1:

Propargylaldehyde diethylacetal is dissolved in THF under argon and cooled to −70° C. Then a solution of butyllithium in hexane is added and stirring continued for about 30 min at −30° C. Then a corresponding compound of formula IV, for example N-methoxy-N-methylacetamide, in THF is added. After 30 min at −30° C., the reaction was quenched by addition of saturated NH$_4$Cl solution. After usual work up one obtained a corresponding compound of formula IX, for example 5,5-diethoxy-pent-3-yn-2-one.

Step B2:

The compound obtained in step B1, for example 5,5-diethoxy-pent-3-yn-2-one, and a corresponding compound of formula VI-a, for example 2-hexyl-isothiourea hydrobromide, are dissolved under nitrogen in THF. Then triethylamine is added slowly while cooling with an ice bath to keep the temperature at 20° C. The suspension is stirred without cooling for about 5 h. The product obtained, for example 4-diethoxymethyl-2-hexylsulfanyl-6-methyl-pyrimidine, is worked up in usual manner.

Step B3:

A compound obtained in step B2, for example 4-diethoxymethyl-2-hexylsulfanyl-6-methyl-pyrimidine, is dissolved in THF and aqueous H$_2$SO$_4$ and is heated at 50° C. for about 33 h. Then the solution is poured in cold Na$_2$CO$_3$ solution and worked up in conventional manner. One obtained a compound of formula XI, for example 2-hexylsulfanyl-6-methyl-pyrimidine-4-carbaldehyde.

Step B4:

A compound of formula XI, obtained in step B3, for example 2-hexylsulfanyl-6-methyl-pyrimidine-4-carbaldehyde, is dissolved in ethanol and acetic acid. Then a compound of formula II, for example pyrrolidine and sodium cyanoborohydride are added slowly at 20° C. and stirring continued for about 24 h. The reaction mixture is worked up in conventional manner. One obtained a compound of formula Ia, for example 2-hexylsulfanyl-4-methyl-6-pyrrolidin-1-ylmethyl-pyrimidine.

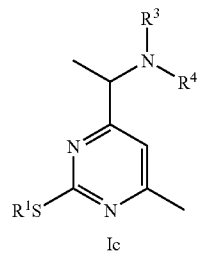

C1) CrO$_3$ in 4 N H$_2$SO$_4$, acetone, 0–20° C.,
C2) TEA, THF, 20° C.,
C3) CrO$_3$ in 4 N H$_2$SO$_4$, acetone, 0–20° C.
C4) Ti(OiPr)$_4$, NaBH$_3$CN, iPrOH, In accordance with scheme 4, compounds of formula Ic may be prepared as follows:

Step C1:

A solution of 3-hexyn-2,5-diol in acetone is cooled in ice under nitrogen. Jones' reagent (45 mmol, 2 M CrO$_3$ in 4 M H$_2$SO$_4$) is added slowly at 5° C. over 2 h. The resulting green solution was decanted from the chromium salts and extracted with AcOEt and sat. NaCl solution. The crude product is purified. One obtained 5-hydroxy-hex-3-yn-2-one of formula XII.

Step C2:

5-Hydroxy-hex-3-yn-2-one and a compound of formula VI-a, for example 2-hexyl-isothiourea hydrobromide, are dissolved in THF. Then triethylamine is added and stirring continued for about 3 h. The obtained product is isolated and purified. One obtained a compound of formula XIII, for example 1-(2-hexylsulfanyl-6-methyl-pyrimidin-4-yl)-ethanol.

Step C3:

A compound, obtained in step C2, for example 1-(2-hexylsulfanyl-6-methyl-pyrimidin-4-yl)-ethanol is dissolved under nitrogen in acetone. Then Jones' reagent, prepared from 20 g CrO$_3$ in 100 mL 4 M H$_2$SO$_4$, is add dropwise. After stirring for about 2 h at 20° C., the resulting solution is isolated and purified in conventional manner. One obtained a compound of formula XIV, for example 1-(2-hexylsulfanyl-6-methyl-pyrimidin-4-yl)-ethanone.

Step C4:

A compound of formula XIV, for example 1-(2-hexylsulfanyl-6-methyl-pyrimidin-4-yl)-ethanone, and a compound of formula II, for example morpholine, are dissolved in tetraisopropyl orthotitanate and heated at about 80° C. for 16 h. The solution is diluted with 2-propanol and treated with sodium cyanoborohydride at about 20° C. for 6 h. The obtained product of formula Ic, for example 4-[1-(2-hexylsulfanyl-6-methyl-pyrimidin-4-yl)-ethyl]-morpholine, is isolated and purified in conventional manner.

As mentioned earlier, the compounds of formula I and their pharmaceutically usable addition salts possess valuable pharmacological properties. It has been found that the compounds of the present invention have an affinity to the GABA$_B$ receptor.

The compounds were investigated in accordance with the tests given hereinafter.

Intracellular Ca$^{2+}$ Mobilization Assay

The Chinese Hamster Ovary (CHO) cells stably expressing human GABA$_B$R1aR$^2$a and Gα16 were seeded at 5×10$^4$ cells/well in the poly-D-lysine treated, 96-well, black/clear- Scheme 4

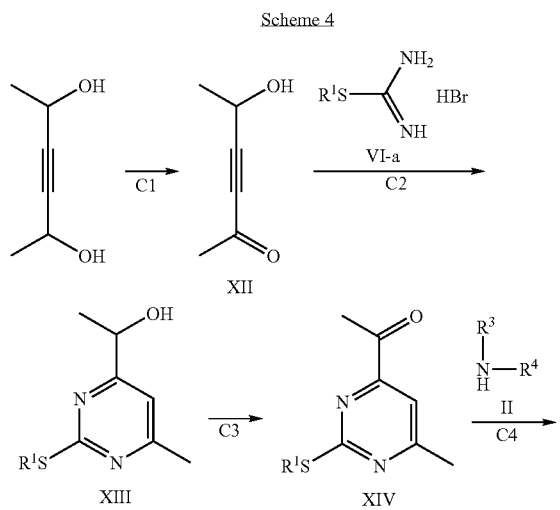

bottomed plates (BD Biosciences, Palo Alto, Calif.). 24 h later, the cells were loaded for 90 min at 37° C. with 4 µM Flou-4 acetoxymethyl ester (Catalog No. F-14202, Molecular Probes, Eugene, Oreg.) in loading buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with loading buffer to remove excess dye and intracellular calcium mobilization, $[Ca^{2+}]_i$ were measured using a Fluorometric Imaging Plate Reader (FLIPR, Molecular Devices, Menlo Park, Calif.) as described previously (Porter et al., *Br. J. Pharmacol.*, 128, 13-20, 1999). The enhancers were applied 15 min before the application of the GABA. For GABA shift assay, concentration-response curves of GABA (0.0003-30 µM) were determined in the absence and presence of 10 µM enhancer. The GABA-shift is defined as Log [$EC_{50}$ (GABA+10 µM enhancer)/$EC_{50}$ (GABA alone)]. The % maximum enhancing effect (% $E_{max}$) potency ($EC_{50}$ value) of each enhancer was determined from concentration-response curve of the enhancer (0.001-30 µM) in the presence of 10 nM (GABA) ($EC_{10}$). Responses were measured as peak increase in fluorescence minus basal, normalized to the maximal stimulatory effect induced by 10 µM GABA alone (considered 100%) and 10 nM GABA alone (considered 0%). The data were fitted with the equation Y=100+(Max −100)/(1+($EC_{50}$/[drug])$^n$) where Max is the maximum effect, $EC_{50}$ the concentration eliciting a half-maximum effect and n the Hill slope.

| | Intracellular $Ca^{2+}$ mobilization Assay in CHO-$GABA_B$R1aR2a-Gα16 cell | | |
|---|---|---|---|
| Example | $E_{max}$ (%) at 10 nM GABA alone = 0% 10 µM GABA alone = 100% | $EC_{50}$ (µM) at 10 nM GABA | GABA shift Log [$EC_{50}$(GABA + 10 µM cp)/ $EC_{50}$(GABA alone)] |
| 1 | 46 | 2.2 | −0.75 |
| 2 | 52 | 1.7 | −0.55 |
| 11 | 41 | 4.2 | −0.60 |
| 16 | 48 | 8.5 | −0.50 |
| 31 | 60 | 9.6 | −0.69 |
| 35 | 62 | 1.8 | −0.92 |
| 37 | 74.2 | 8.2 | −0.76 |
| 38 | 61 | 6.3 | −0.71 |
| 39 | 62 | 6.4 | −0.48 |
| 41 | 60 | 4.1 | −0.86 |
| 43 | 49 | 4.4 | −0.70 |

The present invention also provides pharmaceutical compositions containing compounds of the inventions or pharmaceutically usable acid addition salts thereof and a pharmaceutically acceptable carrier. Such pharmaceutical compositions can be administered in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic excipients. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injectable solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of the invention, e.g. a compound of formula I, and/or a pharmaceutically acceptable acid addition salt thereof and, if desired, one or more therapeutically valuable substances into a galenical administration form together with one or more therapeutically inert carrier.

Compound of the present invention enhance $GABA_B$ receptor activity. Therefore, the present invention also provides method of treating diseases for which enhancement of $GABA_B$ receptors may be beneficial. Such diseases include anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders or gastro-intestinal disorders, and, respectively, for the manufacture of corresponding medicaments.

In particular, the invention provides a method for the treatment of treating depression which comprises administering a therapeutically effective amount of a compound of formula I. In addition, the invention provides a method for the treatment of treating anxiety which comprises administering a therapeutically effective amount of a compound of formula I. The invention also provides a method for the treatment of treating schizophrenia which comprises administering a therapeutically effective amount of a compound of formula I. The invention further provides a method for the treatment of treating epilepsy which comprises administering a therapeutically effective amount of a compound of formula I.

The invention provides a method for the treatment of treating multiple sclerosis which comprises administering a therapeutically effective amount of a compound of formula I. The invention also provides a method for the treatment of treating amyotrophic lateral sclerosis which comprises administering a therapeutically effective amount of a compound of formula I. The invention further provides a method for the treatment of treating cerebral palsy which comprises administering a therapeutically effective amount of a compound of formula I.

The invention provides a method for the treatment of treating spinal cord injury which comprises administering a therapeutically effective amount of a compound of formula I. The invention also provides a method for the treatment of treating neuropathic pain and craving associated with cocaine and nicotine which comprises administering a therapeutically effective amount of a compound of formula I.

The invention provides a method for the treatment of treating panic disorder which comprises administering a therapeutically effective amount of a compound of formula I. The invention also provides a method for the treatment of treating posttraumatic stress disorders which comprises administering a therapeutically effective amount of a compound of formula I. The invention further provides a method for the treatment of treating gastro-intestinal disorders which comprises administering a therapeutically effective amount of a compound of formula I.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of supporsitories, or parenterally, for example, in the form of injection solutions.

The dosage at which a compound of the invention is administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following Examples illustrate the present invention without limiting it. All temperatures are given in degrees Celsius.

Intermediates IV: N-Methoxy-N-methyl-acetamide

N,O-dimethyl-hydroxylamine HCl (100 g, 1025 mmol) was suspended under nitrogen in DCM (1000 mL) and cooled in ice. Triethylamine (300 mL, 2152 mmol) was added slowly, then acetyl chloride (76.5 mL, 1076 mmol) was added slowly, the temperature reached 20° despite ice cooling and slow addition. Stirring without cooling was continued for 30 min. Extraction: 1×DCM, 1×1N HCl, 2× saturated NaCl solution. Distillation at 42° C./20 mbar gave 69 g (65%) of a colorless oil.

Cyclopropanecarboxylic acid methoxy-methyl-amide

N,O-dimethyl-hydroxylamine HCl (40 g, 410 mmol) was suspended under nitrogen in DCM (400 mL) and cooled in ice. Triethylamine (63 mL, 451 mmol) was added slowly, then cyclopropanecarbonyl chloride (41 mL, 451 mmol) was added slowly. Stirring without cooling was continued for 1 h. Extraction: 2×DCM, 1×1 N HCl, 1×NaCl. Distillation: 75° C./20 mbar. One obtained 32.5 g (61%) of a colorless oil.

Intermediates VI: 2-Hexyl-isothiourea hydrobromide

Thiourea (50 g, 657 mmol) and 1-bromohexane (119 mL, 723 mmol) were heated at reflux under nitrogen in ethanol (500 mL) for 20 h. Ethanol was evaporated, and the thick oil stirred in diethyl ether (500 mL). The product precipitated spontaneously. After filtration one obtained 144.5 g (91%) of white crystals, m.p. 75° C.

2-Thio-2-(3,7,9-trimethyl-2,6-decadienyl)pseudo-urea hydrobromide

In analogous manner using (2E,6E)-1-bromo-3,7,9-trimethyl-deca-2,6-diene.

2-(4-Methyl-benzyl)-isothiourea hydrobromide

In analogous manner using 4-methyl-benzylbromide.

2-((E)-3-m-Tolyl-allyl)-isothiourea hydrobromide

In analogous manner using 1-((E)-3-bromo-propenyl)-3-methyl-benzene.

2-(4-tert-Butyl-benzyl)-isothiourea hydrobromide

In analogous manner using 4-tert-butyl-benzylbromide.

2-(3-Phenyl-propyl)-isothiourea hydrobromide

In analogous manner using 1-bromo-3-phenylpropane. One obtained 25.9 g (72%) of a white solid, m.p. 96° C.

2-(1,3-Dimethyl-butyl)-isothiourea hydrobromide

In analogous manner using 2-Bromo-4-methyl-pentane.

2-Butyl-isothiourea hydroiodide

In analogous manner using 1-iodobutane.

2-(4-Phenoxy-butyl)-isothiourea hydrobromide

In analogous manner using 4-phenoxybutyl bromide.

N-Hydroxy-nonanamidine

Octyl cyanide (2 g, 14 mmol) and hydroxylamine hydrochloride (2.495 g, 36 mmol) were dissolved in EtOH (10 mL) and treated with triethylamine (5 mL, 36 mmol) at reflux over night. Extraction: AcOEt/water. Silica gel chromatography: heptane/AcOEt 1:2 afforded a white solid (0.65 g, 26%). MS: m/z=173 (M +H).

Nonanamidine Mesylate

To a solution of N-hydroxy-nonanamidine (0.6 g, 3.48 mmol) in ethanol (5 mL) was added fresh Raney Nickel (0.05 g) and methanesulfonic acid (0.08 ml, 1.26 mmol). The reaction mixture was stirred for 3 h at 20° C. in a hydrogen atmosphere. Filtration over Celite and evaporation afforded a light green oil (0.5 g, 56%). MS: m/z=157 (M+H).

Step A1: 4-Prop-2-ynyl-morpholine

Morpholine (100 ml, 1.148 mol) was dissolved in MeOH (1 L) and cooled in ice under nitrogen, then potassium carbonate (120 g, 0.63 mol) and propargyl bromide (124 mL, 1.148 mol) were added while stirring in ice. Stirring without cooling was continued for 4 h. The white suspension was filtered through paper and the solids were washed with MeOH (100 ml) and the MeOH was carefully evaporated. The white precipitate was suspended in DCM (400 ml), filtered through paper, and carefully evaporated. Finally the oil was distilled at 60° C./16 mbar. One obtained 100 g (70%) of a colorless oil.

Step A2: 5-Morpholin-4-yl-pent-3-yn-2-one

4-Prop-2-ynyl-morpholine (22 g, 176 mmol) was dissolved under nitrogen in THF (40 mL) and cooled to −40° C. Then a 2 M solution of isopropyl magnesium chloride in THF (97 mL, 193 mmol) was added while keeping the temperature below −20° C. Stirring at −40° C. to −30° C. was continued for 30 min. In a separate flask, N-methoxy-N-methylacetamide (20 g, 193 mmol) was dissolved under nitrogen in THF (40 mL) and cooled to −10° C. in ice/MeOH. The Grignard solution prepared above was transferred to the Weinreb amide solution at −10° C. via teflon tubing under slightly positive nitrogen pressure in vessel 1. There was no exotherm. Stirring at −10° C. to 0° C. was continued for 2 h. Ther resulting white suspension was poured on a 1:1-mixture of ice and saturated NH$_4$Cl solution (400 mL). Extraction: 2×AcOEt, 1× saturated NaCl solution. One obtained a yellow oil (26.1 g, 89%). Chromatography on silica gel in heptane/ethyl acetate 1:2 gave 19.4 g (66%) of a brown oil which was distilled in the Kugelrohr at 130° C./0.2 mbar. One obtained 15.8 g (53%) of a yellow oil.

Step A3:

EXAMPLE 1

4-(2-Hexylsulfanyl-6-methyl-pyrimidin-4-ylmethyl)-morpholine

5-Morpholin-4-yl-pent-3-yn-2-one (1 g, 6 mmol) and 2-hexyl-isothiourea hydrobromide (1.06 g, 7 mmol) were dissolved under nitrogen in DMF (10 mL), then N,N-diisopropyl ethylamine (4.1 mL, 24 mmol) was added and stirring at the room temperature continued for 18 hours.

DMF was evaporated. The product was extracted with AcOEt (2×50 mL), saturated solution of NH$_4$Cl (2×50 mL), dried and concentrated. The residue was purified by flash chromatography on an aminated silica gel column with a heptane/ethyl acetate gradient. One obtained 440 mg (24%) of a yellow liquid. MS: m/z=310 (M+H).

EXAMPLE 2

4-(6-Methyl-2-pentylsulfanyl-pyrimidin-4-ylmethyl)-morpholine

In analoguous manner using N-pentylisothiuronium hydrochloride. One obtained 260 mg (29%) of a brown oil. MS: m/z=296 (M+H).

EXAMPLE 3

4-[6-Methyl-2-((2E,6E)-3,7,9-trimethyl-deca-2,6-dienylsulfanyl)-pyrimidin-4-ylmethyl]-morpholine In analoguous manner using 2-thio-2-(3,7,9-trimethyl-2,6-decadienyl)pseudo-urea hydrobromide. One obtained 300 mg (35%) of a colorless oil. MS: m/z=404 (M+H).

EXAMPLE 4

4-[6-Methyl-2-((E)-3-phenyl-allylsulfanyl)-pyrimidin-4-ylmethyl]-morpholine

In analoguous manner using 2-((E)-3-phenyl-allyl)-isothiourea. One obtained 300 mg (34%) of a colorless oil. MS: m/z=342 (M+H).

EXAMPLE 5

4-[2-(4-Methoxy-benzylsulfanyl)-6-methyl-pyrimidin-4-ylmethyl]-morpholine

In analoguous manner using 2-(p-methoxybenzyl)-2-thiopseudourea. One obtained 414 mg (40%) of a colorless oil. MS: m/z=346 (M+H).

EXAMPLE 6

4-[6-Methyl-2-(4-methyl-benzylsulfanyl)-pyrimidin-4-ylmethyl]-morpholine

In analoguous manner using 2-(4-methyl-benzyl)-isothiourea hydrobromide. One obtained 427 mg (48%) of a colorless oil. MS: m/z=330 (M+H).

EXAMPLE 7

4-[6-Methyl-2-((E)-3-m-tolyl-allylsulfanyl)-pyrimidin-4-ylmethyl]-morpholine

In analoguous manner using 2-((E)-3-m-tolyl-allyl)-isothiourea. One obtained 100 mg (20%) of a yellow oil. MS: m/z=356 (M+H).

EXAMPLE 8

4-[6-Methyl-2-(4-phenoxy-butylsulfanyl)-pyrimidin-4-ylnethyl]-morpholine

In analoguous manner using 2-(4-phenoxy-butyl)-isothiourea hydrobromide. One obtained 100 mg (18%) of a yellow oil. MS: m/z=374 (M+H).

EXAMPLE 9

4-(2-Butylsulfanyl-6-methyl-pyrimidin-4-ylmethyl)-morpholine

In analoguous manner using 2-butyl-isothiourea hydroiodide. One obtained 100 mg (23%) of a yellow oil. MS: m/z=282 (M+H).

EXAMPLE 10

4-[2-(1,3-Dimethyl-butylsulfanyl)-6-methyl-pyrimidin-4-ylmethyl]-morpholine

In analogous manner using 2-(1,3-dimethyl-butyl)-isothiourea hydrobromide. One obtained 100 mg (20%) of a yellow oil. MS: m/z=310 (M+H).

EXAMPLE 11

4-[2-(4-tert-Butyl-benzylsulfanyl)-6-methyl-pyrimidin-4-ylmethyl]-morpholine In analogous manner using 2-(4-tert-butyl-benzyl)-isothiourea hydrobromide. One obtained 200 mg (32%) of a yellow oil. MS: m/z=372 (M+H).

EXAMPLE 12

4-[6-Methyl-2-(3-phenyl-propylsulfanyl)-pyrimidin-4-ylmethyl]-morpholine

In analogous manner using 2-(3-phenyl-propyl)-isothiourea hydrobromide. One obtained 300 mg (48%) of a yellow oil. MS: m/z=344 (M+H).

EXAMPLE 13

4-(2-Ethylsulfanyl-6-methyl-pyrimidin-4-ylmethyl)-morpholine

In analogous manner using 2-ethyl-2-thiopseudourea hydrobromide. One obtained 1.5 g (55%) of a yellow oil. MS: m/z=254 (M+H).

EXAMPLE 14

4-(6-Methyl-2-octyl-pyrimidin-4-ylmethyl)-morpholine

5-Morpholin-4-yl-pent-3-yn-2-one (0.2 g, 1.2 mmol) and nonanamidine mesylate (0.5 g, 3 mmol) were dissolved in MeOH (5 ml) and treated with a 5.4 M solution of sodium methylate in MeOH (1.33 ml, 7 mmol) at reflux for 15 h. MeOH was evaporated, and the mixture extracted with AcOEt and water. The crude product was purified by chromatography on Si-amine with a heptane/AcOEt gradient of 100:0 to 80:20 affording a light yellow oil (0.2 g, 54%). MS: m/z=306.4 (M+H).

Step A4: 4-(2-Ethanesulfonyl-6-methyl-pyrimidin-4-ylmethyl)-morpholine 4-(2-Ethylsulfanyl-6-methyl-pyrimidin-4-ylmethyl)-morpholine (2 g, 6.4 mmol) was dissolved in MeOH (20 mL) and treated with potassium monopersulfate triple salt (5.57 g, 9 mmol) for 2 h. Filtered, filtrate stirred with 10% aqueous NaHSO₃ solution (10 mL) for 5 min and then extracted with AcOEt/H₂O. Chromatography on silica gel with a gradient heptane/AcOEt 3:2 to 2:3 afforded a colorless oil (0.6 g, 36%). MS: m/z=286 (M+H).

Step A5:

EXAMPLE 15

(3,5-Bis-trifluoromethyl-benzyl)-(4-methyl-6-morpholin-4-ylmethyl-pyrimidin-2-yl)-amine 4-(2-Ethanesulfonyl-6-methyl-pyrimidin-4-ylmethyl)-morpholine (0.2 g, 0.55 mmol) and 3,5-bis(trifluoromethyl) benzylamine (0.51 g, 2.1 mmol) dissolved in THF (2 mL) were stirred at 20° C. overnight. Evaporated and extracted with AcOEt (40 ml) and NaHCO₃ (40 ml). Chromathography on silica gel in AcOEt/heptane 2:1 gave a light yellow oil (60 mg, 20%). MS: m/z=435 (M+H).

Step B1: 5,5-Diethoxy-pent-3-yn-2-one

Propargylaldehyde diethylacetal (40 g, 312 mmol) was dissolved in THF (200 mL) under argon and cooled to −70° C. Then a 1.6 M solution of n-butyllithium in hexane (234 mL, 374 mmol) was added and stirring continued for 30 min at −30° C. Then N-methoxy-N-methylacetamide (38.6 g, 374 mmol) in THF (10 mL) was added. After 30 min at −30° C., the reaction was quenched by addition of saturated NH₄Cl solution (20 mL). The product was extracted with AcOEt (2×200 mL), saturated solution of NH₄Cl (2×200 mL), dried and concentrated. Chromatography on silica gel with a heptane/ethyl acetate gradient 100:0 to 95:5 gave 38.5 g (72%) of a colorless oil. GC/MS: m/z=232(M).

5,5-Diethoxy-1,1,1-trifluoro-pent-3-yn-2-one 3,3-Diethoxy-1-propyne (10 mL, 70 mmol) was dissolved under argon in THF (200 mL) and cooled to −70° C. Then a 1.6 M solution of n-butyllithium in hexane (48 mL, 77 mmol) was added slowly at −70° C., then allowed to warm to −30° C. and stirred at −30° C. for 30 min, then cooled again to −70° C. Ethyl trifluoroacetate (9.2 mL, 77 mmol) was added in one portion at −70° C. (the temperature rose to −50°) then stirred without cooling until −30° C. was reached, then quenched with sat. NH₄Cl solution (20 mL). Extraction: 2×AcOEt, 1× sat. NH₄Cl sat., 1× sat. NaCl. Chromatography on silica gel in heptane/ethyl acetate 5:1 afforded 4.94 g (31%) of an orange oil. GC/MS: m/z=223 (M−H).

1-Cyclopropyl-4,4-diethoxy-but-2-yn-1-one 3,3-Diethoxy-1-propyne (10 mL, 70 mmol) was dissolved under argon in THF (150 mL) and cooled to −70° C. Then a 1.6 M solution of n-butyllithium in hexane (48 mL, 77 mmol) was added slowly at −70° C., then allowed to warm to −30° C. and stirred at −30° C. for 30 min, then cooled again to −70° C. Cyclopropanecarboxylic acid methoxy-methyl-amide (10 g, 77 mmol) was added at once at −70° C. (the temperature rose to −50°) then stirred without cooling until 0° C. was reached, then quenched with sat. NH₄Cl solution (20 mL). Extraction: 2×AcOEt, 1× sat. NH₄Cl, 1× sat. NaCl. The crude brown oil (15 g) was purified by chromatography on silica gel in heptane/ethyl acetate 10:1. One obtained 6 g (43%) of a yellowish oil. MS: m/z=151 (M).

4,4-Diethoxy-but-2-ynal 3,3-Diethoxy-1-propyne (10 mL, 70 mmol) was dissolved under argon in THF (50 mL) and cooled to −70° C. Then a 1.6 M solution of n-butyllithium in hexane (48 mL, 77 mmol) was added slowly at −70° C., then allowed to warm to −40° C. and stirred at −40° C. for 15 min, then cooled again to −70° C. DMF (6 mL, 77 mmol) was added at −70° C., then stirred without cooling until −10° C. were reached, then quenched with sat. NH₄Cl solution (10 mL). Extraction: AcOEt, sat. NH₄Cl solution. Chromatography: heptane/ethyl acetate 95:5. One obtained 300 mg (2.7%) of a volatile colorless oil, which was directly used in the next step.

Step B2: 4-Diethoxymethyl-2-hexylsulfanyl-6-methyl-pyrimidine 5,5-Diethoxy-pent-3-yn-2-one (15 g, 88 mmol) and 2-hexyl-isothiourea hydrobromide (23 g, 97 mmol) were dissolved under nitrogen in THF (150 mL). Then triethylamine (27 mL, 194 mmol) was added slowly while cooling with an ice bath to keep the temperature at 20° C. The suspension was stirred without cooling for 5 h. The product was extracted with AcOEt, sat. NH$_4$Cl solution, dried and concentrated. The residue was purified by silica gel chromatography in heptane/AcOEt 20:1. One obtained 22.3 g (80%) of a colorless oil and 2.8 g of a yellow by-product.

4-Diethoxymethyl-2-hexylsulfanyl-6-trifluoromethyl-pyrimidine 5,5-Diethoxy-1,1,1-trifluoro-pent-3-yn-2-one (2 g, 8.9 mmol) and 2-hexyl-isothiourea hydrobromide (2.4 g, 9.8 mmol) were dissolved under nitrogen in THF (20 mL). Then triethylamine (2.7 mL, 19.6 mmol) was added slowly. The reaction was exothermic (40° C.). The suspension was stirred for 4 h at 20° C. The product was extracted with AcOEt, sat. NH$_4$Cl solution, dried and concentrated. The residue was purified by silica gel chromatography in heptane/AcOEt 20:1. One obtained 2.5 g (76%) of a colorless oil. MS: m/z=367 (M+H).

4-Cyclopropyl-6-diethoxymethyl-2-hexylsulfanyl-pyrimidine

Cyclopropyl-4,4-diethoxy-but-2-yn-1-one (2 g, 10 mmol) and 2-hexyl-isothiourea hydrobromide (2.7 g, 11.2 mmol) were dissolved under nitrogen in THF (20 mL). Then triethylamine (3.1 mL, 22.4 mmol) was added slowly. The reaction was slightly exothermic (28° C.). The suspension was stirred for 5 h at 20° C. The product was extracted with AcOEt, sat. NH$_4$Cl solution, dried and concentrated. The residue was purified by silica gel chromatography in heptane/ethyl acetate 95:5. One obtained 2.86 g (83%) of a colorless oil. MS: m/z=339 (M+H).

4-Diethoxymethyl-2-hexylsulfanyl-pyrimidine (4,4-Diethoxy-but-2-ynal and 2-hexyl-isothiourea hydrobromide (300 mg, 1.9 mmol) (509 g, 2.1 mmol) were dissolved under nitrogen in THF (3 mL). Then triethylamine (0.6 mL, 4.2 mmol) was added. Then suspension was stirred at 20° C. overnight. The product was extracted with AcOEt, sat. NH$_4$Cl solution, dried and concentrated. The residue was purified by silica gel chromatography in heptane/ethyl acetate 95:5. One obtained 260 mg (45%) of a colorless oil. MS: m/z=299 (M+H).

Step B3: 2-Hexylsulfanyl-6-methyl-pyrimidine-4-carbaldehyde

4-Diethoxymethyl-2-hexylsulfanyl-6-methyl-pyrimidine (19 g, 60.8 mmol) was dissolved in THF (100 mL) and 4 N aqueous H$_2$SO$_4$ (100 mL) and heated at 50° C. for 33 h. Poured in cold 10% Na$_2$CO$_3$ solution (400 mL) and extracted with ethyl acetate and a sat. solution of NaCl. The crude oil was purified by silica gel chromatography with a heptane/DCM gradient of 100:0 to 67:33. One obtained 10.7 g (74%) of a yellow oil.

2-Hexylsulfanyl-6-trifluoromethyl-pyrimidine-4-carbaldehyde

4-Diethoxymethyl-2-hexylsulfanyl-6-trifluoromethyl-pyrimidine(1.6 g, 4.4 mmol) was stirred in trfluoroacetic acid (15 mL) and water (1.5 mL) for 10 h at 20° C. The reaction mixture was evaporated to dryness and the residue extracted with ethyl acetate, sat. Na$_2$CO$_3$ solution and sat. NaCl solution. One obtained 1.18 g (92%) of a yellow oil. MS: m/z=311 (M+H+H$_2$O, hydrate).

6-Cyclopropyl-2-hexylsulfanyl-pyrimidine-4-carbaldehyde

4-Cyclopropyl-6-diethoxymethyl-2-hexylsulfanyl-pyrimidine (2.7 g, 8 mmol) was dissolved in THF (13 mL) and 4 N HCl (13 mL) and stirred at 20° C. for 19 h. The reaction mixture was poured in cold 10% Na$_2$CO$_3$ (100 mL) and extracted twice with AcOEt and once with sat. NaCl solution. The crude product was purified by chromatography on silica gel in heptane/DCM with a gradient of 100:0 to 67:33. One obtained 2 g (94%) of a yellow oil, which solidified upon standing in the fridge. MS: m/z=264 (M).

2-Hexylsulfanyl-pyrimidine-4-carbaldehyde

4-Diethoxymethyl-2-hexylsulfanyl-pyrimidine (250 mg, 0.8 mmol) was stirred in THF (5 mL) and 4 N HCl (5 mL) at 20° C. for 64 h. The reaction mixture was poured in cold 10% Na$_2$CO$_3$ and extracted twice with AcOEt and once with sat. NaCl solution.

The crude product was purified by chromatography on silica gel in heptane/AcOEt 10:1. One obtained 138 mg (73%) of a yellow oil. MS: m/z=224 (M).

Step B4:

EXAMPLE 16

2-Hexylsulfanyl-4-methyl-6-pyrrolidin-1-ylmethyl-pyrimidine

2-Hexylsulfanyl-6-methyl-pyrimidine-4-carbaldehyde (0.1 g, 0.42 mmol) was dissolved in ethanol (1 mL) and acetic acid (0.1 mL). Then pyrrolidine (0.07 mL, 1 mmol) and sodium cyanoborohydride (26 mg, 0.4 mmol) were added slowly at 20° C. and stirring continued for 24 h. The reaction mixture was evaporated to dryness and dissolved in a minimal amount of DMF (0.8 mL) and directly purified by preparative HPLC chromatography on a YMC combiprep ODS-AQ column (75×20 mm iD, S-5 µM, 12 nm) with an acetonitrile-water gradient. One obtained 34.7 mg (28%) of a yellow liquid. MS: m/z=294 (M+H).

EXAMPLE 17

1-(2-Hexylsulfanyl-6-methyl-pyrimidin-4-yl-methyl)-pyrolidin-3-ol

In analoguous manner using 3-pyrrolidinol. MS: m/z=310 (M+H).

EXAMPLE 18

[1-(2-Hexylsulfanyl-6-methyl-pyrimidin-4-ylmethyl)-pyrrolidin-3-yl]-dimethyl-amine In analoguous manner using 3-(dimethylamino)pyrrolidine. MS: m/z=337 (M+H).

EXAMPLE 19

2-Hexylsulfanyl-4-methyl-6-piperidin-1-ylmethyl-pyrimidine

In analoguous manner using piperidine. MS: m/z=308 (M+H).

EXAMPLE 20

8-(2-Hexylsulfanyl-6-methyl-pyrimidin-4-ylmethyl)-1,4-dioxa-8-aza-spiro [4.5]decane In analoguous manner using 1,4 dioxa-8-azaspiro(4.5) decane. MS: m/z=366 (M+H).

EXAMPLE 21

1-(2-Hexylsulfanyl-6-methyl-pyrimidin-4-ylmethyl)-piperidine-3-carboxylic acid amide In analoguous manner using nipecotamide. MS: m/z=351 (M+H).

EXAMPLE 22

4-(3,5-Dimethyl-piperidin-1-ylmethyl)-2-hexylsulfanyl-6-methyl-pyrimidine

In analoguous manner using 3,5-dimethyl-piperidine. MS: m/z=336 (M+H).

EXAMPLE 23

1-(2-Hexylsulfanyl-6-methyl-pyrimidin-4-ylmethyl)-piperidin-4-ol

In analoguous manner using 4-hydroxypiperidine. MS: m/z=324 (M+H).

EXAMPLE 24

2-(2-Hexylsulfanyl-6-methyl-pyrimidin-4-ylmethyl)-decahydro-isoquinoline

In analoguous manner using decahydroisoquinoline. MS: m/z=362 (M+H).

EXAMPLE 25

1-(2-Hexylsulfanyl-6-methyl-pyrimidin-4-ylmethyl)-4-methyl-[1,4]diazepane

In analoguous manner using N-methylhomopiperazine. MS: m/z=337 (M+H).

EXAMPLE 26

2-(2-Hexylsulfanyl-6-methyl-pyrimidin-4-ylmethyl)-1,2,3,4-tetrahydro-isoquinoline In analoguous manner using 1,2,3,4-tetrahydroisoquinoline. MS: m/z=356 (M+H).

EXAMPLE 27

1-(2-Hexylsulfanyl-6-methyl-pyrimidin-4-ylmethyl)-azepane

In analoguous manner using hexamethyleneimine. MS: m/z=322 (M+H).

EXAMPLE 28

(2S,6R)-4-(2-Hexylsulfanyl-6-methyl-pyrimidin-4-ylmethyl)-2,6-dimethyl-morpholine In analoguous manner using cis-2,6-dimethylmorpholine. MS: m/z=338 (M+H).

EXAMPLE 29

1-(2-Hexylsulfanyl-6-methyl-pyrimidin-4-ylmethyl)-piperidin-3-ol

In analoguous manner using 3-hydroxypiperidine. MS: m/z=324 (M+H).

EXAMPLE 30

4-(4-Ethyl-piperazin-1-ylmethyl)-2-hexylsulfanyl-6-methyl-pyrimidine

In analoguous manner using N-ethylpiperazine. MS: m/z=337 (M+H).

EXAMPLE 31

2-Hexylsulfanyl-4-methyl-6-(2-methyl-piperidin-1-ylmethyl)-pyrimidine

In analoguous manner using 2-methylpiperidine. MS: m/z=322 (M+H).

EXAMPLE 32

1-[4-(2-Hexylsulfanyl-6-methyl-pyrimidin-4-ylmethyl)-[1,4]diazepan-1-yl]-ethanone In analoguous manner using N-acetylhomopiperazine. MS: m/z=365 (M+H).

EXAMPLE 33

4-(2-Hexylsulfanyl-6-methyl-pyrimidin-4-ylmethyl)-[1,4]oxazepane

In analoguous manner using homomorpholine hydrochloride. MS: m/z=323 (M+H).

EXAMPLE 34

4-(3,5-Dimethyl-piperazin-1-ylmethyl)-2-hexylsulfanyl-6-methyl-pyrimidine

In analoguous manner using 2,6-dimethylpiperazine. MS: m/z=337 (M+H).

EXAMPLE 35

(1S,5S)-3-(2-Hexylsulfanyl-6-methyl-pyrimidin-4-ylmethyl)-1,2,3,4,5,6-hexahydro-1,5-methano-pyrido[1,2-a][1,5]diazocin-8-one In analoguous manner using (−)-cytisine. MS: m/z=413 (M+H).

EXAMPLE 36

1-Benzyl-4-(2-hexylsulfanyl-6-methyl-pyrimidin-4-ylmethyl)-[1,4]diazepane

In analoguous manner using 1-benzyl-hexahydro-1,4diazepine. MS: m/z=413 (M+H).

EXAMPLE 37:

4-(2,6-Dimethyl-piperidin-1-ylmethyl)-2-hexylsulfanyl-6-methyl-pyrimidine

2-Hexylsulfanyl-6-methyl-pyrimidine-4-carbaldehyde (0.2 g, 1 mmol) and 2,6-dimethylpiperidine (0.23 mL, 2 mmol) were dissolved in tetraisopropyl orthotitanate (0.5 mL) and stirred at 20° C. for 1 h. The solution was diluted with 2-propanol (5 mL) and treated with sodium cyanoborohydride (105 mg, 2 mmol) at 20° C. for 20 h. Water (1 mL) was added, and the resulting precipitate filtered off and evaporated. The product was extracted with AcOEt, sat. $NH_4Cl$ solution, dried and concentrated. The residue was purified by preparative HPLC chromatography on a YMC combiprep ODS-AQ column (75×20 mm iD, S-5 µM, 12 nm) with an acetonitrile-water gradient. One obtained 37 mg (36%) of a colorless liquid. MS: m/z=336 (M+H).

EXAMPLE 38

4-(cis-2,6-Dimethyl-piperidin-1-ylmethyl)-2-hexyl-sulfanyl-6-methyl-pyrimidine

In analoguous manner using cis-2,6-dimethylpiperidine. MS: m/z=336 (M+H).

EXAMPLE 39

4-(2-Hexylsulfanyl-6-trifluoromethyl-pyrimidin-4-ylmethyl)-morpholine

2-Hexylsulfanyl-6-trifluoromethyl-pyrimidine-4-carbaldehyde (0.5 g, 1.7 mmol) and morpholine (0.16 mL, 1.9 mmol) were dissolved in ethanol (5 mL) and acetic acid (0.5 mL) and treated with borane-pyridine complex (0.19 mL, 1.9 mmol) for 4 h at 20° C. The reaction mixture was evaporated to dryness. Extraction: 2×AcOEt, 1×10% aqueous $Na_2CO_3$. One obtained a mixture of the expected product and the reduced aldehyde which was more polar. This mixture was separated by chromatography on Si-amine from Silicycle with a gradient of heptane/ethyl acetate from 10:1 up to 1:1. Gave 220 mg (35%) of a colorless oil. MS: m/z=364 (M+H).

EXAMPLE 40

4-(6-Cyclopropyl-2-hexylsulfanyl-pyrimidin-4-ylmethyl)-morpholine

In analogous manner from 6-cyclopropyl-2-hexylsulfanyl-pyrimidine-4-carbaldehyde. One obtained 342 mg (54%) of a colorless oil. MS: m/z=336 (M+H).

EXAMPLE 41

4-(2-Hexylsulfanyl-6-ethyl-pyrimidin-4-ylmethyl)-morpholine

In analogous manner from 6-ethyl-2-hexylsulfanyl-pyrimidine-4-carbaldehyde. One obtained a colorless oil. MS: m/z=324 (M+H).

EXAMPLE 42

4-(2-Hexylsulfanyl-pyrimidin-4-ylmethyl)-morpholine

In analogous manner from 2-hexylsulfanyl-pyrimidine-4-carbaldehyde. One obtained 62 mg (36%) of a colorless oil. MS: m/z=296 (M+H).

Step C1: 5-Hydroxy-hex-3-yn-2-one

A solution of 3-hexyn-2,5-diol (5 mL, 45 mmol) in acetone (50 mL) was cooled in ice under nitrogen. Jones' reagent (22 ml, 45 mmol, 2 M $CrO_3$ in 4 M $H_2SO_4$) was added slowly at 5° C. over 2 h. The resulting green solution was decanted from the chromium salts and extracted with AcOEt and sat. NaCl solution. The crude product was purified by chromatography on silica gel with a heptane/AcOEt gradient. One obtained 2.2 g (45%) of a colorless oil.

Step C2: 1-(2-Hexylsulfanyl-6-methyl-pyrimidin-4-yl)-ethanol

5-Hydroxy-hex-3-yn-2-one (2 g, 18 mmol) and 2-hexyl-isothiourea hydrobromide (5.2 g, 21 mmol) were dissolved in THF (10 mL). Then the triethylamine (5.5 mL, 40 mmol) was added and stirring continued for 3 h. The reaction was slightly exothermic. The mixture was extracted with AcOEt and sat. $NH_4Cl$ solution. The crude product was purified by chromatography on silica gel with a heptane/AcOEt gradient. One obtained 2.8 g (61%) of a light yellow oil. MS: m/z=254 (M)

Step C3: 1-(2-Hexylsulfanyl-6-methyl-pyrimidin-4-yl)-ethanone 1-(2-Hexylsulfanyl-6-methyl-pyrimidin-4-yl)-ethanol (2.2 g, 8.65 mmol) was dissolved under nitrogen in acetone (20 mL). Then 2 M Jones' reagent prepared from 20 g $CrO_3$ in 100 mL 4 M $H_2SO_4$ (6.5 mL, 13 mmol) was add dropwise. After stirring for 2 h at 20° C., the resulting green solution was decanted from the chromium salts and extracted with AcOEt and sat. NaCl solution. The crude product was purified by chromatography on silica gel with a heptane/AcOEt gradient. One obtained 960 mg (44 %) of white crystals. MS: m/z=252 (M).

Step C4:

EXAMPLE 43

4-[1-(2-Hexylsulfanyl-6-methyl-pyrimidin-4-yl)-ethyl]-morpholine 1-(2-Hexylsulfanyl-6-methyl-pyrimidin-4-yl)-ethanone (200 mg, 0.79 mmol) and morpholine (138 µL, 1.58 mol) were dissolved in tetraisopropyl orthotitanate (0.5 mL) and heated at 80° C. for 16 h. The brown solution was diluted with 2-propanol (5 mL) and treated with sodium cyanoborohydride (32 mg, 0.5 mmol) at 20° C. for 6 h. Extraction: 2×AcOEt, 2× sat. $NH_4Cl$ solution. Chromatography: Si-amine, heptane/ethyl acetate 85:15. One obtained 86 mg (34%) of a yellow oil. MS: m/z=324 (M+H).

The invention claimed is:
1. A compound of the formula

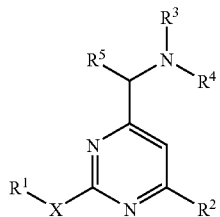

I wherein
X is —S— or —NH—;
$R^1$ is alkyl, alkenyl, arylalkyl, arylalkenyl or aryl-O-alkyl, and wherein the aryl groups are optionally substituted by one or more substituents selected from the group consisting of lower alkyl, lower alkoxy, halogen and lower halogen-alkyl;
$R^2$ is hydrogen, lower alkyl or cycloalkyl;

R³/R⁴ together with the N-atom to which they are attached form a non aromatic 5, 6 or 7 membered ring, which optionally contains in addition to the N-atom, one additional heteroatom selected from the group consisting of O, S and N, and wherein the ring is optionally substituted by hydroxy, lower alkyl, lower alkoxy, —NR₂, —CONR₂, —CO-lower alkyl or benzyl; or R³/R⁴ together with the N-atom to which they are attached form a heterocyclic ring system, containing two or three rings and which optionally contains one or two additional heteroatoms selected from the group consisting of N and O, and which has no more than 20 carbon atoms;

R is hydrogen or lower alkyl;

R⁵ is hydrogen or alkyl;

or a pharmaceutically suitable acid addition salt thereof.

2. A compound of claim 1, wherein X is —S—.

3. A compound of claim 2, wherein R³ and R⁴ form together with the N-atom to which they are attached, a five, six, or seven membered ring which optionally contains an additional N-heteroatom or O-heteroatom, and which is unsubstituted or substituted by hydroxy, lower alkyl, lower alkoxy, —NR₂, —CONR₂, —CO-lower alkyl or benzyl.

4. A compound of claim 3, wherein R³ and R⁴ form together with the N-atom to which they are attached, a five or six membered ring which optionally contains an additional N-heteroatom or O-heteroatom, and which is unsubstituted or substituted by hydroxy, lower alkyl, lower alkoxy, —NR₂, —CONR₂, —CO-lower alkyl or benzyl.

5. A compound of claim 4, wherein R³ and R⁴ form together with the N-atom to which they are attached a morpholine ring.

6. A compound of claim 5, wherein R¹ is alkyl or alkenyl.

7. A compound of claim 6, selected from the group consisting of
  4-(2-Hexylsulfanyl-6-methyl-pyrimidin-4-ylmethyl)-morpholine;
  4-(6-Methyl-2-pentylsulfanyl-pyrimidin-4-ylmethyl)-morpholine;
  4-(2-Butylsulfanyl-6-methyl-pyrimidin-4-ylmethyl)-morpholine;
  4-[2-(1,3-Dimethyl-butylsulfanyl)-6-methyl-pyrimidin-4-ylmethyl]-morpholine;
  4-(2-Ethylsulfanyl-6-methyl-pyrimidin-4-ylmethyl)-morpholine;
  4-(6-Methyl-2-octyl-pyrimidin-4-ylmethyl)-morpholine;
  (2S,6R)-4-(2-Hexylsulfanyl-6-methyl-pyrimidin-4-ylmethyl)-2,6-dimethyl-morpholine;
  4-(2-Hexylsulfanyl-6-trifluoromethyl-pyrimidin-4-ylmethyl)-morpholine;
  4-(6-Cyclopropyl-2-hexylsulfanyl-pyrimidin-4-ylmethyl)-morpholine;
  4-(2-Hexylsulfanyl-6-ethyl-pyrimidin-4-ylmethyl)-morpholine;
  4-(2-Hexylsulfanyl-pyrimidin-4-ylmethyl)-morpholine;
  4-[1(2-Hexylsulfanyl-6-pyrimidin-4-yl)-ethyl]-morpholine; and
  4-[6-Methyl-2-((2E,6E)-3,7,9-trimethyl-deca-2,6-dienyl-sulfanyl)-pyrimidin-4-ylmethyl]-morpholine.

8. A compound of claim 5, wherein R¹ is arylalkyl, arylalkenyl, or aryl-O-alkyl.

9. A compound of claim 8, which is selected from the group consisting of
  4-[6-Methyl-2-((E)-3-phenyl-allylsulfanyl)-pyrimidin-4-ylmethyl]-morpholine;
  4-[6-Methyl-2-((E)-3-m-tolyl-allylsulfanyl)-pyrimidin-4-ylmethyl]-morpholine;
  4-[2-(4-Methoxy-benzylsulfanyl)-6-methyl-pyrimidin-4-ylmethyl]-morpholine;
  4-[6-Methyl-2-(4-methyl-benzylsulfanyl)-pyrimidin-4-ylmethyl]-morpholine:
  4-[2-(4-tert-Butyl-benzylsulfanyl)-6-methyl-pyrimidin-4-ylmethyl]-morpholine
  4-[6-Methyl-2-(3-phenyl-propylsulfanyl)-pyrimidin-4-ylmethyl]-morpholine; and
  4-[6-Methyl-2-(4-phenoxy-butylsulfanyl)-pyrimidin-4-ylmethyl]-morpholine.

10. A compound of claim 4, wherein R¹ is alkyl.

11. A compound of claim 10 wherein R³ and R⁴ form together with the N-atom to which they are attached a pyrrolidine ring.

12. A compound of claim 11, selected from the group consisting of
  2-Hexylsulfanyl-4-methyl-6-pyrrolidin-1-ylmethyl-pyrimidine;
  1-(2-Hexylsulfanyl-6-methyl-pyrimidin-4-ylmethyl)-pyrrolidin-3-ol; and
  [1-(2-Hexylsulfanyl-6-methyl-pyrimidin-4-ylmethyl)-pyrrolidin-3-yl]-dimethyl-amine.

13. A compound of claim 10, wherein R³ and R⁴ form together with the N-atom to which they are attached a piperidine ring.

14. A compound of claim 13, selected from the group consisting of
  2-Hexylsulfanyl-4-methyl-6-piperidin-1-ylmethyl-pyrimidine;
  1-(2-Hexylsulfanyl-6-methyl-pyrimidin-4-ylmethyl)-piperidine-3-carboxylic acid amide;
  4-(3,5-Dimethyl-piperidin-1-ylmethyl)-2-hexylsulfanyl-6-methyl-pyrimidine;
  1-(2-Hexylsulfanyl-6-methyl-pyrimidin-4-ylmethyl)-piperidin-4-ol;
  1-(2-Hexylsulfanyl-6-methyl-pyrimidin-4-ylmethyl)-piperidin-3-ol;
  2-Hexylsulfanyl-4-methyl-6-(2-methyl-piperidin-1-ylmethyl)-pyrimidine;
  4-(2,6-Dimethyl-piperidin-1-ylmethyl)-2-hexylsulfanyl-6-methyl-pyrimidine; and
  4-(cis-2,6-Dimethyl-piperidin-1-ylmethyl)-2-hexylsulfanyl-6-methyl-pyrimidine.

15. A compound of claim 10, wherein R³ and R⁴ form together with the N-atom to which they are attached a piperazine ring.

16. A compound of claim 15, which is
  4-(4-Ethyl-piperazin-1-ylmethyl)-2-hexylsulfanyl-6-methyl-pyrimidine; or 4-(3,5-Dimethyl-piperazin-1-ylmethyl)-2-hexylsulfanyl-6-methyl-pyrimidine.

17. A compound of claim 3, wherein R³ and R⁴ form together with the N-atom to which they are attached, a seven membered ring which optionally contains an additional N-heteroatom or O-heteroatom, and which is unsubstituted or substituted by hydroxy, lower alkyl, lower alkoxy, —NR₂, —CONR₂, —CO-lower alkyl or benzyl.

18. A compound of claim 17, selected from the group consisting of
  1-(2-Hexylsulfanyl-6-methyl-pyrimidin-4-ylmethyl)-4-methyl-[1,4]diazepane;
  1-(2-Hexylsulfanyl-6-methyl-pyrimidin-4-ylmethyl)-azepane;
  1-[4-(2-Hexylsulfanyl-6-methyl-pyrimidin-4-ylmethyl)-[1,4]diazepan-1-yl]-ethanone;
  4-(2-Hexylsulfanyl-6-methyl-pyrimidin-4-ylmethyl)-[1,4]oxazepane; and
  1-Benzyl-4-(2-hexylsulfanyl-6-methyl-pyrimidin-4-ylmethyl)-[1,4]diazepane.

19. A compound of claim 2, wherein R³/R⁴ together with the N-atom to which they are attached form a heterocyclic ring system, containing two or three rings and which optionally contains one or two additional heteroatoms selected from the group consisting of N and O, and which has no more than 20 carbon atoms.

20. A compound of claim 19, selected from the group consisting of
8-(2-Hexylsulfanyl-6-methyl-pyrimidin-4-ylmethyl)-1,4-dioxa-8-aza-spiro[4.5]decane;
2-(2-Hexylsulfanyl-6-methyl-pyrimidin-4-ylmethyl)-decahydro-isoquinoline;
2-(2-Hexylsulfanyl-6-methyl-pyrimidin-4-ylmethyl)-1,2,3,4-tetrahydro-isoquinoline; and
(1S,5S)-3-(2-Hexylsulfanyl-6-methyl-pyrimidin-4-ylmethyl)-1,2,3,4,5,6-hexahydro-1,5-methano-pyrido[1,2-α][1,5]diazocin-8-one.

21. A compound of claim 1, wherein X is —NH—.

22. A compound of claim 21, which is
(3,5-Bis-trifluoromethyl-benzyl)-(4-methyl-6-morpholin-4-ylmethyl-pyrimidin-2-yl)-amine.

23. A compound of claim 1, wherein $R^5$ is hydrogen.

24. A pharmaceutical composition comprising a therapeutically effective amount of a compound of formula I

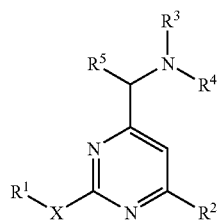

wherein
X is —S— or —NH—;
$R^1$ is alkyl, alkenyl, arylalkyl, arylalkenyl or aryl-O-alkyl, and wherein the aryl groups are optionally substituted by one or more substituents selected from the group consisting of lower alkyl, lower alkoxy, halogen and lower halogen-alkyl;
$R^2$ is hydrogen, lower alkyl or cycloalkyl;
$R^3/R^4$ together with the N-atom to which they are attached form a non aromatic 5, 6 or 7 membered ring, which optionally contains in addition to the N-atom, one additional heteroatom selected from the group consisting of O, S and N, and wherein the ring is optionally substituted by hydroxy, lower alkyl, lower alkoxy, —$NR_2$, —$CONR_2$, —CO-lower alkyl or benzyl; or
$R^3/R^4$ together with the N-atom to which they are attached form a heterocyclic ring system, containing two or three rings and which optionally contains one or two additional heteroatoms selected from the group consisting of N and O, and which has no more than 20 carbon atoms;
R is hydrogen or lower alkyl;
$R^5$ is hydrogen or alkyl;
or a pharmaceutically suitable acid addition salt thereof and a pharmaceutically acceptable carrier.

* * * * *